United States Patent [19]
Momose

[11] Patent Number: 5,795,490
[45] Date of Patent: Aug. 18, 1998

[54] MAGNETIC HEAD DAMAGE EVALUATION METHOD AND APPARATUS THEREFOR

[75] Inventor: Satoru Momose, Tokyo, Japan

[73] Assignee: NEC Corporation, Tokyo, Japan

[21] Appl. No.: 828,913

[22] Filed: Mar. 28, 1997

[30] Foreign Application Priority Data

Mar. 31, 1996 [JP] Japan ..................... 8-104374

[51] Int. Cl.$^6$ ....................... B44C 1/22
[52] U.S. Cl. .............. 216/22; 156/345; 216/84; 216/85
[58] Field of Search ............... 216/22, 59, 60, 216/84, 85; 156/345 LC

[56] References Cited

U.S. PATENT DOCUMENTS

| | | | |
|---|---|---|---|
| 5,329,689 | 7/1994 | Azuma et al. | 216/22 X |
| 5,566,075 | 10/1996 | Syouji et al. | 216/22 X |
| 5,624,581 | 4/1997 | Ihrke et al. | 216/22 |

FOREIGN PATENT DOCUMENTS 6-60466  3/1994  Japan.

*Primary Examiner*—William Powell
*Attorney, Agent, or Firm*—Laff, Whitesel, Conte & Saret, Ltd.

[57] ABSTRACT

Nitric acid is used to etch the air-bearing-surface (alumina titanium carbide) of a slider, the air-bearing-surface overcoat and adhesive layer formed thereon being worn out, sa as to reduce the optical reflectance of the region where the air-bearing-surface substrate is exposed. The air-bearing-surface of the slider is optically imaged and the resulting image processed by a computer to determine the surface area of the region where both the adhesive layer and the air-bearing-surface overcoat are worn out, having reduced optical reflectance. Then, the adhesive layer is removed by means of hydrofluoric acid treatment and etching is again done with nitric acid to create another region with a reduced optical reflectance, enabling determination of the surface area of the region over which only the air-bearing-surface overcoat is worn out.

8 Claims, 5 Drawing Sheets

Fig. 1
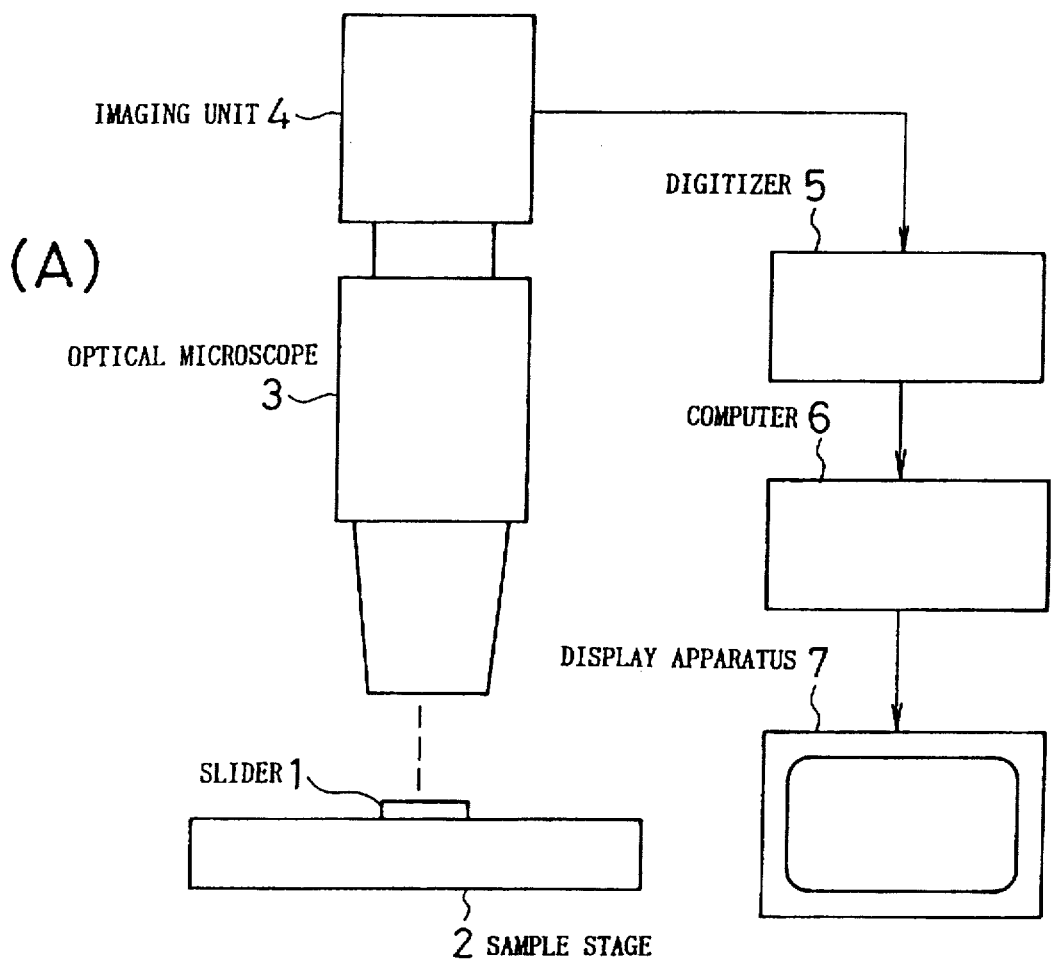
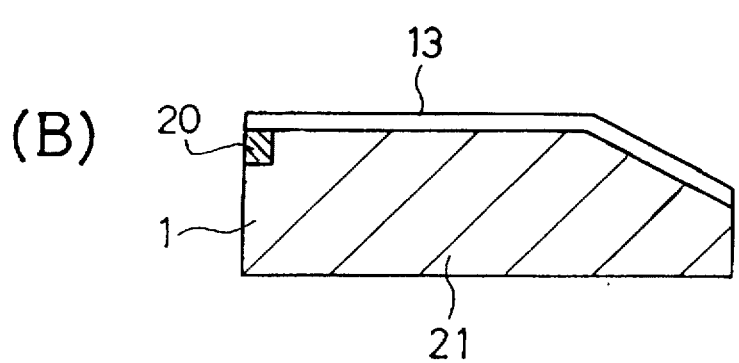

Fig.2
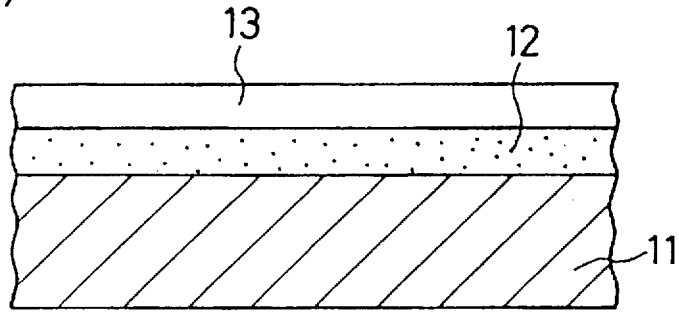
(A)
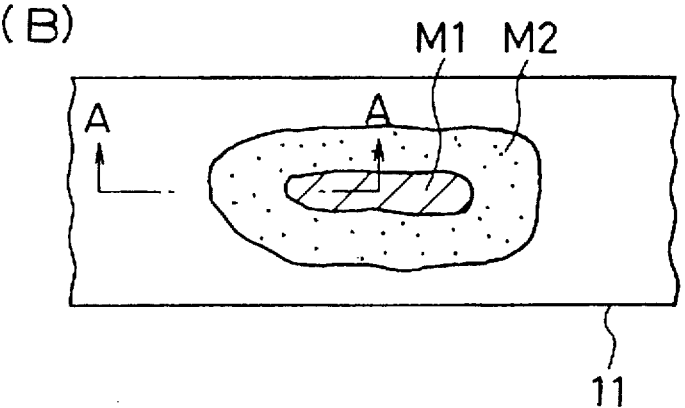
(B)
11  SLIDER AIR BEARING SURFACE
12  SILICON-CONTAINNING ADHESIVE LAYER
13  CARBON-CONTAINNING AIR-BEARING-SURFACE OVERCOAT
M1  REGION WHERE BOTH THE AIR-BEARING-SURFACE OVERCOAT AND ADHESIVE LAYER ARE WORN OUT
M2  REGION WHERE ONLY THE AIR-BEARING-SURFACE OVERCOAT IS WORN OUT Fig. 4
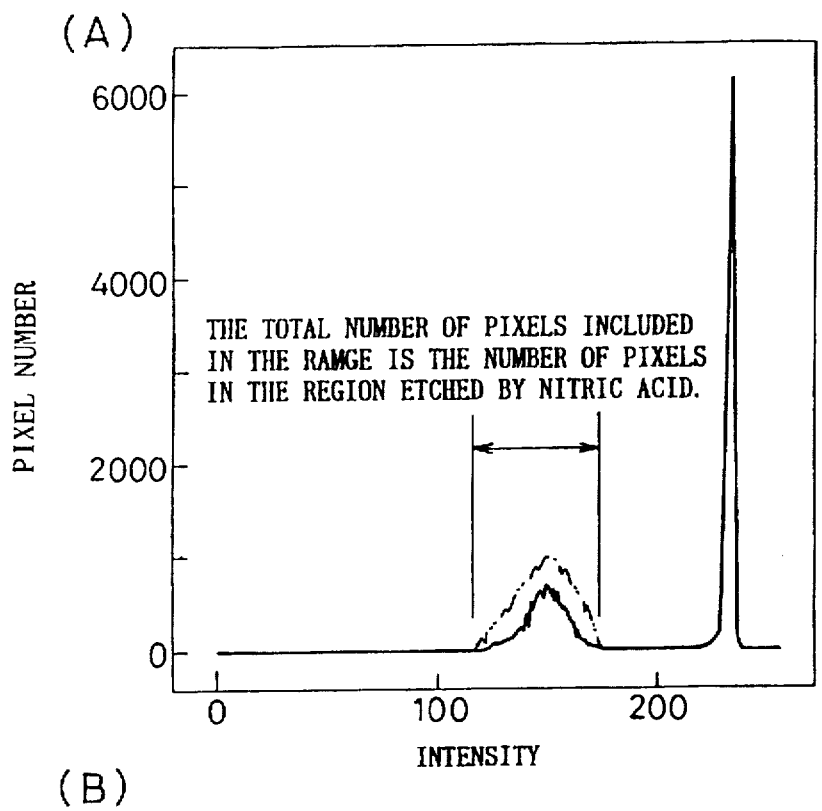
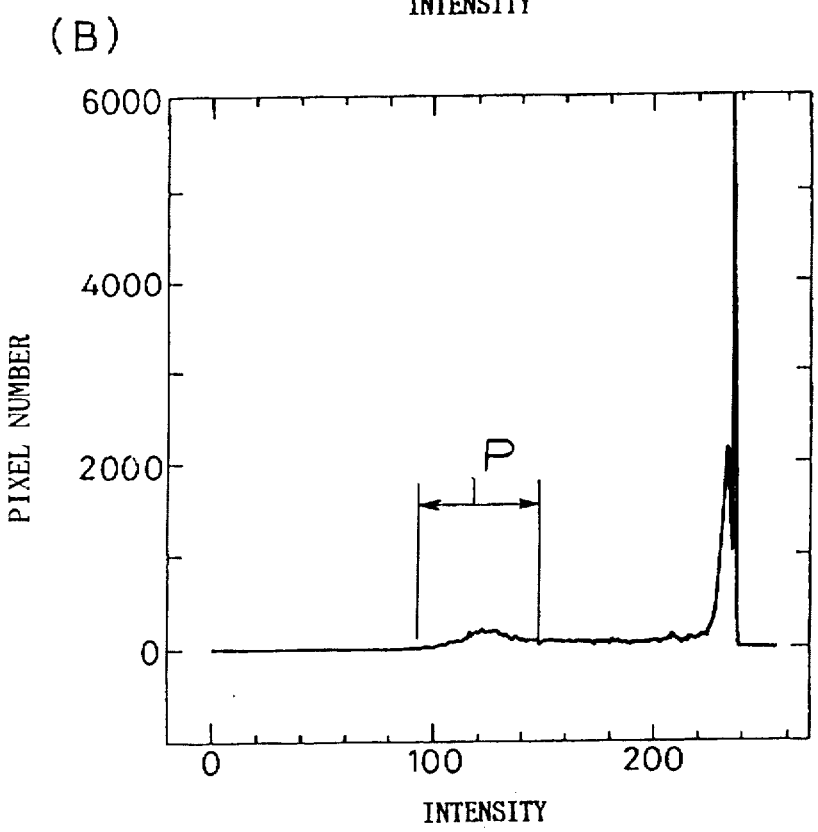

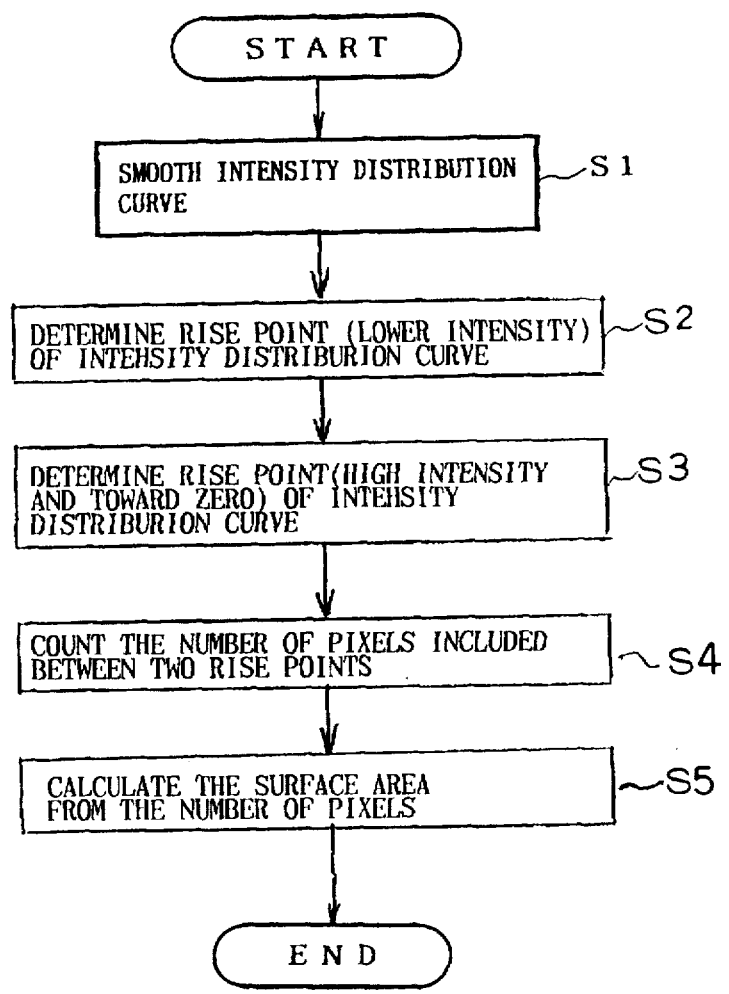

MAGNETIC HEAD DAMAGE EVALUATION METHOD AND APPARATUS THEREFOR

BACKGROUND OF THE INVENTION

1. Field of the Invention

The present invention relates to a slider including a magnetic head thereon, which is used in a magnetic recording apparatus, and more specifically to a method and apparatus for the purpose of evaluating damage occurring to the air-bearing-surface of the slider having the magnetic head thereon in a magnetic recording apparatus when recording and playback are performed with the slider in proximity to or in physical contact with a recording medium surface.

2. Description of Related Art

With an increase in recording density in magnetic recording apparatuses, such as magnetic disk apparatuses, the configuration that has come into use is one in which the air-bearing-surface of the slider including a magnetic head thereon and the recording surface of the magnetic disk medium are in proximity to each other as possible it can.

However, when these elements are brought into proximity, the mutual interaction between a air-bearing-surface of the slider having the magnetic head and the recording surface of the magnetic disk becomes large, the magnetic disk or magnetic head becoming damaged, resulting in a deterioration in the recording and playback characteristics or a shortening of the life of the apparatus.

For this reason, there is a need to evaluate the damage incurred on the air-bearing-surface of the slider having the magnetic head thereon, which is a constituent element of the magnetic disk apparatus, and to manufacture a slider carrying a magnetic head thereon capable of withstanding such treatment with less damage incurred.

Because an air-bearing-surface-overcoat is generally provided on an air-bearing-surface of a slider carrying a magnetic head thereon, via and intervening adhesive layer, if these layers become worn so as to expose a surface of the slider substrate itself, the magnetic head provided on the slider will tend to suffer from the above-noted deterioration in recording and playback characteristics and a shortening of its life.

It is therefore necessary to understand the wear condition of these adhesive layer and surface-protection overcoat. A technique for understanding of such sliders wear condition has been disclosed, for example, in the Japanese Unexamined Patent Publication No. 6-60466, according to which disclosure it can be envisioned by the technique of observing the surface of the slider with a continuously autofocusing microscope can.

However, the above-noted film layers which are formed on the surface of the slider are extremely thin, the thickness is within 10 mm, and are often colorless and transparent, so that by mere observation of the air-bearing-surface of the slider using a microscope it would be impossible to ascertain the wear condition thereof.

Because of the above, a method used in the past is that at first remove the overcoat is a part of the air-bearing-surface region and after a durability test of the slider by measuring the border formed between the remaining region of the overcoat and the region from which the overcoat had been removed, using stylus-type step profilometer, so as to understand the wear condition of the air-bearing-surface overcoat.

However, with this method, if as a result of the durability test of the slider, wear does not occur at that border, it is not possible to know the wear.

It is also not possible using this method to distinguish between the condition in which only the air-bearing-surface overcoat is worn and the condition in which the wear extends from the air-bearing-surface overcoat to the adhesive layer, thereby a hindrance presents to obtaining a clear and quantitative evaluation of the wear.

In view of the above-noted drawbacks in the prior art, an object of the present invention is to provide a slider surface damage evaluation method and evaluation apparatus which are capable of making a clear and quantitative evaluation of the damage to the air-bearing-surface overcoat and adhesive layer of a slider carrying the magnetic head.

SUMMARY OF THE INVENTION

To achieve the above-noted object, the present invention has the basic technical constitution described below.

More specifically, the air-bearing-surface of the slider which opposes a recording surface of a recording medium, and being onto the surface thereof, is formed an air-bearing-surface overcoat. According to the present invention, to evaluate the region in which both the air-bearing-surface overcoat and an adhesive layer are worn out, the method comprises of three steps: the first step in which the air-bearing surface of the slider including the magnetic head, the air-bearing-surface overcoat formed thereon, being worn and exposed, is etched to reduce its optical reflectance; a second step in which the air-bearing-surface of the slider is optically imaged so as to obtain and image which includes a region having a high optical reflectance and a region having a low optical reflectance; and a third step in which, at least from the region having a low optical reflectance image, a condition of a worn out region formed on the surface-overcoat of the slider is recognized.

For a slider carrying a magnetic head that is provided with an air-bearing-surface overcoat formed on a slider air-bearing-surface substrate with interposing an adhesive layer therebetween, a slider surface damage evaluation method for evaluation of damage to a surface of a slider including a magnetic head, onto the air-bearing-surface, which opposes a recording surface of a recording medium, and is formed an air-bearing-surface overcoat with interposing an adhesive layer therebetween, by recognition of the wear condition of the surface-overcoat, the method comprises: the a first step in which the slider is etched and the exposed slider substrate region in the air-bearing-surface, where both the air-bearing-surface overcoat and the adhesive layer are worn out, is reduced it's optical reflectance; a second step in which the air-bearing-surface of the slider is optically imaged so as to obtain an image which includes a region having a high optical reflectance and a region having a low optical reflectance; a third step in which, from the images, at least the surface area of the part having a low optical reflectance is calculated as the surface area over which both the adhesive layer and the air-bearing-surface overcoat are worn out; a fourth step in which the adhesive layer exposed by losing the air-bearing-surface overcoat is removed from the air-bearing-surface of the slider surface; a fifth step in which the exposed slider air-bearing-surface substrate by removing the adhesive layer, is etched so as to reduce its optical reflectance; a sixth step in which the air-bearing-surface of the slider is optically imaged so as to obtain an image which includes a region having a high optical reflectance and a region having a low optical reflectance; and a seventh step in which from the images, at least the surface area of the part having a low optical reflectance is calculated as the worn out area of the surface-overcoat.

A damage evaluation apparatus according to the present invention has an imaging means which images the slider air-bearing-surface processed so as to have a lowered optical reflectance, a digitizer that converts an image signal obtained from the above-noted imaging method to pixel data which corresponds to the intensity thereof, and a computer which processes the thus-obtained pixel data so as to calculate the surface area of the above damage. In this case, it is desirable that the computer have a function which counts the pixels distributed in a region of low intensity and calculates the above-noted damaged surface area.

DESCRIPTION OF THE DRAWINGS

FIG. 1 (A) is a block diagram which shows the conceptual configuration of a damage evaluation apparatus according to the present invention, and FIG. 1(B) shows a sectional view of a normal slider including a magnetic head therein.

FIGS. 2(A) and 2(B) are cross-sectional views of the air-bearing-surface of a slider and a plan view of the damage condition thereof.

FIGS. 4(A) and 4(B) are graphs which show intensity distribution curves obtained from a damaged surface of the slider.

FIG. 5 is a flowchart which shows the process of calculating the damaged surface area using a computer.

DETAILED DESCRIPTION OF THE INVENTION

Figure 3:
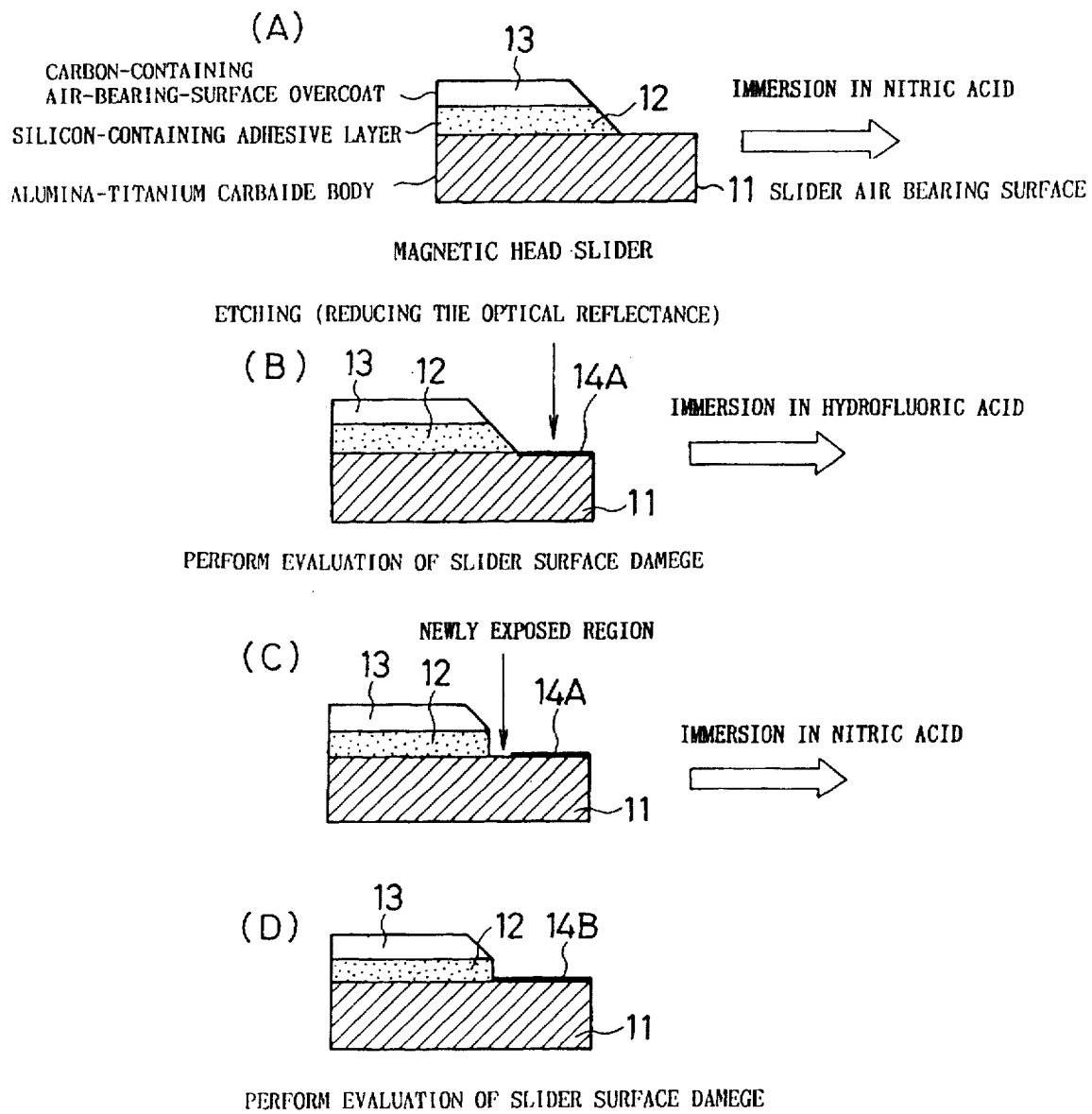
FIGS. 3[(A)–(D)] is an enlarged cross-sectional view along in the direction A—A indicated in FIG. 2, provided to illustrate the damage evaluation method.

Preferred embodiments of present invention will now be described, with reference being made to the relevant accompanying drawings.

FIG. 1 is a block diagram which shows the conceptual configuration of an air-bearing-surface damage evaluating apparatus used for a slider including a magnetic head according to the present invention.

A slider 1 is placed on top of the sample stage 2, with its air-bearing-surface facing upward. Immediately above this slider 1 is located an optical microscope 3, which optically magnifies the air-bearing-surface of the slider 1.

The optical microscope 3 is provided with an imaging unit 4, which outputs an optical image of the air-bearing-surface of the slider as a electrically converted image signal.

A digitizer 5 digitizes the image signal from the imaging unit 4 in extremely small units of surface area, and outputs the resulting digital signal to a computer 6. The computer 6 performs image processing, which will be described later, and displays the damage condition of the air-bearing-surface of the slider 1 obtained from that image processing on a display apparatus 7.

As shown in FIG. 1(B), a slider 1 normally comprises a substrate 21 made of a suitable metallic material and a magnetic head 20, usually provided at a rear end portion of the slider 1 and the air-bearing-surface of the base portion 21 of the slider, which opposes to a recording medium, is covered with an air-bearing-surface overcoat 13.

Next, the evaluation method used in the damage evaluating apparatus which is shown in FIG. 1 will be described. Consider the case in which the slider under test, as shown in the partial cross-sectional view of the air-bearing-surface in FIG. 2 (A), has an alumina, titanium carbide body, and an air-bearing-surface overcoat 13 made from a carbon-containing material, with an interneving adhesive layer 12 of a silicon-containing material, is deposited on it's air-bearing-surface.

By performing a durability test on such a slider, as shown in the plan view shown in FIG. 2 (B), a worn out region M2 occurs in the air-bearing-surface overcoat 13 on the air-bearing-surface 11 of the slider, and a region M1, where both the air-bearing-surface overcoat 13 and the lay 12, are worn out, also occurs.

In the subsequent steps, the wear condition of the air-bearing-surface overcoat 13 and the adhesive layer 12 will be determined.

FIG. 3 is an enlarged cross-sectional view of the part shown in FIG. 2 (B) by the line A—A.

First, as shown in FIG. 3 (A), a slider which has undergone a durability test which has caused partial wear thereof is immersed in nitric acid having high concentration for a short period. By doing this, as shown in FIG. 3 (B), the air-bearing-surface 11 made of alumina-titanium carbide, which is exposed because of the wearing away of the air-bearing-surface overcoat 13 and the adhesive layer 12, is etched by the nitric acid, the optical reflectance of a part 14A thereof being thereby reduced.

Therefore, by placing this slider on the sample stage 2 shown in FIG. 1, optically imaging it using the optical microscope 3, and processing the resulting image signal using the digitizer 5, the characteristics shown by a solid line in FIG. 4 (A) are obtained.

These characteristics show the pixel number corresponding to each intensity at the air-bearing-surface of the slider.

From these characteristics, it is possible to discern that the part with high intensity is the remaining part of the air-bearing-surface overcoat 13 and adhesive layer 12, and that the part with a low intensity and a somewhat larger pixel number is the part that was etched by the nitric acid, that is, the region of both the air-bearing-surface overcoat 13 and the adhesive layer 12 were worn out.

Therefore, by processing this etched region using the computer 6 to perform processing to be described later, it is possible to calculate the above worn out substrate area, that is, the surface area of region M1 which is shown in FIG. 2 (B).

On the other hand, as indicated by the characteristics shown in FIG. 4 (B), there are cases in which the pixel number for relatively high intensity are a little bit increased from the base line but still relatively be in a low level comparing with that of the obvious etched region, indicated by symbol P in FIG. 4(B).

In this case, it is assumed that there are some regions on the surface of the protecting film layer, in which some irregular configuration or fine concaved-convexed portions are existing on the surface thereof.

Therefore, in the present invention, the above-mentioned data may be ignored, but it would be preferable that a certain level of a threshold value should be introduced previously, so as to discriminate the difference between the true etched air-bearing-surface substrate and the mere irregular configuration thereof.

Next, after removing the above-noted slider from the sample stage 2, it is immersed in hydrofluoric acid having a concentration of 50 wt % or lower. By doing this, as shown in FIG. 3 (C), only the silicon material adhesive layer 12 which is exposed because it loses the cover of air-bearing-surface 13, is dissolved, the result being that the air-bearing-surface substrate 11 which had been covered by only the adhesive layer 12 is newly exposed.

Then, the slider is once again immersed as noted above in nitric acid, the result being that, as shown in FIG. 3 (D), the newly exposed alumina-titanium carbide surface is etched, the optical reflectance of this etched region 14B being thereby reduced.

This slider is again placed on the sample stage which is shown in FIG. 1(A) and imaged by the optical microscope 3 and the imaging unit 4, the resulting image signal being processed by the digitizer 5, so as to obtain the characteristics indicated by a broken in FIG. 4 (A).

That is, these characteristics indicate an increase in pixel number in the part having a low intensity, this portion corresponding to the newly etched surface area. Therefore, by processing the region using the computer 6 in the same manner as in the previous step, it is possible to calculate the region over which only the air-bearing-surface overcoat 13 is worn out, that is, the surface area of the region M2 which is shown in FIG. 2 (B).

A durability test was performed on a slider having a silicon film of thickness 5 nm as an adhesive layer and an amorphous carbon film of thickness 5 nm as an air-bearing-surface overcoat.

Then, the slider was etched by immersion for 30 minutes in 70% nitric acid and washed in water, after which it was evaluated by the damage evaluating apparatus shown in FIG. 1(A), the result was $1.74 \times 10^4$ $\mu m^2$ as the etched area.

Then the slider was immersed for 2.5 minutes in 3.5% hydrofluoric acid to remove the silicon adhesive layer and etched the region from which the adhesive layer had just been removed, in the same manner using nitric acid, the resulting surface area was $7.37 \times 10^4$ $\mu m^2$.

From these results, it can be seen that the surface area of the region over which both the air-bearing-surface overcoat and the adhesive layer were worn out was $1.74 \times 10^4$ $\mu m^2$ and that the surface area of the region over which only the air-bearing-surface overcoat was worn out was $7.37 \times 10^4$ $\mu m^2$, so that the surface area of the region over which the air-bearing-surface overcoat was worn out but over which the adhesive layer remained was the difference of these two values, which is $5.63 \times 10^4$ $\mu m^2$.

The processing performed by the computer 6 to calculate the etched surface area based on the intensity distributions shown in FIG. 4 (A) obtained from the digitizer 5 will now be described.

FIG. 5 is a flowchart of this processing. First, the thus-obtained intensity distribution curve is smoothed (step S1).

Then, from the intensity zero towards the maximum value, the first point at which the intensity distribution curve determined in step S1 rises is determined (step S2). Thereafter, from the intensity maximum towards zero, the first point at which the intensity distribution curve determined in step S1, rises, is determined (Step S3).

At this point, the total number of pixels from the intensity at the rising point determined at step S2 to the rising point determined at step S3 is counted (step S4). Finally, the number of pixels obtained in step S5 is multiplied by the separately determined surface area occupied by one pixel to calculate the etched surface area (step S5).

Thus, by displaying on the display apparatus, for example, and enlarged view of the air-bearing-surface of the slider with the region in which both the air-bearing-surface overcoat and the adhesive layer are worn out, the region in which only the air-bearing-surface overcoat is worn out, and the region in which not even the air-bearing-surface overcoat is worn, under the condition showing different colors for each respective region, it is possible to recognize as a pattern image the wear condition of the air-bearing-surface overcoat and adhesive layer. By adding to this a display of the value of the above-noted wear surface area, it is possible to make this recognition quantitatively as well.

As an example of a method of applying such wear evaluation results to an actual slider manufacturing process, the following type of manufacturing process can be used.

(1) Fabricate head elements on an alumina-titanium carbide wafer.

(2) Slice the wafer so that head elements are arranged in a single row.

(3) Polish and process the surfaces of the row, that is, the air-bearing-surfaces of the slider.

(4) Coat the air-bearing-surfaces with an adhesive layer and then with an air-bearing-surface overcoat.

(5) Slice the row of head elements into individual slider elements including the magnetic head.

(6) Bond wires to each of the individual head elements of the slider mount the slider on a gimbal and connect the wires.

Thus, at the point at which the above-noted step (2) is completed, some of the head elements are sliced apart so as to form a slider, processed by step (3) to form the sliders to form the playback apparatus, and then subjected to a durability test. Then, the above-described damage evaluation is performed on these sliders. If the results of this evaluation are that the air-bearing-surface overcoat or adhesive layer does not have sufficient durability, rows produced by the same process as that row are re-processed to apply an air-bearing-surface overcoat and an adhesive layer.

For example, the films that had been formed can be removed by oxygen plasma etching, and reformed using a set of conditions different from the original conditions. Then, a part of the heads thus fabricated can be sliced apart and subjected to a durability test and damage evaluation as described above. By repeating this process thereafter, it is possible to fabricate sliders with superior durability. By employing this type of manufacturing process, compared to the case in which the air-bearing-surface overcoat and adhesive layers of all the sliders are reapplied, it is possible to achieve a reduction in the labor required for optimizing the film depositing condition by 20%.

In the case in which the materials used to form the air-bearing-surface overcoat and the adhesive layer of the slider are different from those noted above, in place of the above-noted nitric acid and hydrofluoric acid, it is possible to make an embodiment of the present invention which achieves the intended effect of the present invention by using an etching or removal fluid that selectively etches each of the materials. Additionally, the process used for processing of the image signal of the slider obtained from imaging unit is not limited to that described above.

For example, one simple method which can be used is that of performing level comparison of the digital signal obtained from the image signal using a plurality of threshold values, and displaying each of the resulting levels as a different color to enable an understanding of the wear condition. It is also possible to obtain an approximate value of the surface area by counting the pixels at the display apparatus.

While the forgoing embodiment was described for the case of a slider over the air-bearing-surface of which is formed an air-bearing-surface overcoat with an intervening adhesive layer, it is also possible to apply the present invention to the case of a slider having just a single airbearing-surface overcoat, obtaining thereby a clear and quantitative understanding of the damage thereto caused by wear of the air-bearing-surface overcoat.

According to the present invention as described in detail above, the air-bearing-surface of a slider, the air-bearing-surface overcoat formed thereon being worn and exposed, is etched to reduce its optical reflectance, the air-bearing-surface of the slider then being optically imaged so as to obtain an image which includes a region having a high optical reflectance and a region having a low optical reflectance, after which, from these images, at least the surface area of the region having a low optical reflectance is calculated as the surface area of the region where the air-bearing-surface overcoat is worn out, thereby enabling the attainment of a clear and quantitative understanding of the wear condition of the air-bearing-surface overcoat of the air-bearing-surface of the slider.

Thus, by using the above-noted present invention, it is possible to fabricate a slider having high reliability and long life with a reduced amount of labor.

What is claimed is:

1. A slider surface damage evaluation method for evaluation of damage to a slider, an air-bearing-surface of which opposes a recording surface of a recording medium, and is formed an air-bearing-surface overcoat on it, by recognition of the wear condition of said air-bearing-surface overcoat, said method comprising:

a first step in which said air-bearing-surface of said slider including said slider, said air-bearing-surface overcoat formed thereon, being worn is etched so as to reduce its optical reflectance of exposed air-bearing-surface substance;

a second step in which said air-bearing-surface of said slider is optically imaged so as to obtain an image which includes a region having a high optical reflectance and a region having a low optical reflectance; and a third step in which, at least from said region having a low optical reflectance image, a condition of a worn out region formed on said air-bearing-surface overcoat of said slider is recognized.

2. A slider surface damage evaluation method according to claim 1, wherein, at said third step, at least the surface area of said part having a low optical reflectance is calculated so as to obtain actual surface area at the region where said air-bearing-surface formed on said slider, is worn out.

3. A slider surface damage evaluation method according to claim 1, wherein said base material of said slider air-bearing-surface is an alumina-titanium carbide material and said air-bearing-surface overcoat is a carbon-containing material, and further wherein a liquid used to etch said air-bearing-surface thereof is nitric acid.

4. A slider surface damage evaluation method for evaluation of damage to a slider, air-bearing-surface of which opposes a recording surface of a recording medium, and is formed an air-bearing-surface overcoat onto it with interposing an adhesive layer therebetween, by recognition of the wear condition of said air-bearing-surface overcoat, said method comprising:

a first step in which said air-bearing-overcoat of said slider including said slider, said air-bearing-surface overcoat and said adhesive layer formed thereon, being worn, is etched so as to reduce the optical reflectance of exposed air-bearing-surface substrate;

a second step in which said air-bearing-surface of said slider is optically imaged so as to obtain an image which includes a region having a high optical reflectance and a region having a low optical reflectance;

a third step in which, from said images, at least the surface area of the part having a low optical reflectance is calculated as the surface area over which both the adhesive layer and the air-bearing-surface overcoat are worn;

a fourth step in which the adhesive layer exposed by losing cover of the air-bearing-surface overcoat, is removed from said air-bearing-surface of said slider surface;

a fifth step in which said exposed air-bearing-surface of said slider by removing of said adhesive layer, is etched so as to lower its optical reflectance;

a sixth step in which said air-bearing-surface of said slider is optically imaged so as to obtain an image which includes a region having a high optical reflectance and a region having a low optical reflectance; and a seventh step in which from said images, at least said surface area of the region having a low optical reflectance is calculated as the surface area of the region where the air-bearing-surface overcoat is worn out.

5. A slider surface damage evaluation method according to claim 4, wherein the surface area of the region in which said adhesive layer is worn out, is calculated by subtracting the surface area of the region over which both said air-bearing-surface overcoat and said adhesive layer are worn out from the surface area of the region over which the surface-protecting layer is worn out.

6. A slider surface damage evaluation method according to claim 4, wherein said air-bearing-surface substrate of said slider is composed of alumina-titanium carbide material, said adhesive layer is composed of a silicon-containing material, and said surface-protecting layer is composed of a carbon-containing material, and further wherein a liquid used to etch said air-bearing-surface is nitric acid and a liquid used to remove said adhesive layer is hydrofluoric acid.

7. A slider damage evaluation apparatus comprising:

a means for imaging a damaged air-bearing-surface of a slider including a slider processed so as to have a reduced optical reflectance;

a digitizer that converts an image signal obtained from said imaging method to pixel data which corresponds to an intensity thereof; and a computer which processes said obtained pixel data so as to calculate a surface area of said damaged portion of said air-bearing-surface of said slider.

8. A slider damage evaluation apparatus according to claim 7, wherein said computer comprises a function which counts the pixels distributed in a region of low intensity and calculates said damaged surface area.

* * * * *